United States Patent
Schmid et al.

(10) Patent No.: US 9,943,696 B2
(45) Date of Patent: Apr. 17, 2018

(54) PROCESS FOR SUPPLYING AN ELECTRICAL ENERGY CONVERTING IMPLANT WITH ELECTRICAL ENERGY

(71) Applicant: Fraunhofer-Gesellschaft zur Förderung der Angewandten Forschung E.V., München (DE)

(72) Inventors: Helmut Schmid, Freudenstadt (DE); Wilhelm Eckl, Karlsruhe (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 0 days.

(21) Appl. No.: 15/514,559

(22) PCT Filed: Sep. 30, 2015

(86) PCT No.: PCT/EP2015/072556
§ 371 (c)(1),
(2) Date: Mar. 27, 2017

(87) PCT Pub. No.: WO2016/050845
PCT Pub. Date: Apr. 7, 2016

(65) Prior Publication Data
US 2017/0216608 A1    Aug. 3, 2017

(30) Foreign Application Priority Data

Sep. 30, 2014   (DE) ................. 10 2014 219 815

(51) Int. Cl.
| A61N 1/00 | (2006.01) |
| A61N 1/378 | (2006.01) |
| A61N 1/362 | (2006.01) |

(52) U.S. Cl.
CPC .......... *A61N 1/3785* (2013.01); *A61N 1/362* (2013.01)

(58) Field of Classification Search
CPC .............................. A61N 1/362; A61N 1/3785
See application file for complete search history.

(56) References Cited

U.S. PATENT DOCUMENTS

| 3,563,245 A | 2/1971 | McLean |
| 3,788,772 A | 1/1974 | Noble et al. |
| 4,102,610 A | 7/1978 | Taboada et al. |
| 5,879,375 A | 3/1999 | Larson, Jr. et al. |
| 6,632,169 B2 | 10/2003 | Korakianitis et al. |
| 2008/0262562 A1 | 10/2008 | Roberts et al. |
| 2009/0171404 A1 | 7/2009 | Irani et al. |
| 2009/0281600 A1 | 11/2009 | Lemieux |
| 2010/0076247 A1* | 3/2010 | Zilbershlag ......... A61M 1/1031 600/17 |
| 2012/0059389 A1 | 3/2012 | Larson et al. |

(Continued)

OTHER PUBLICATIONS

International Search Report for corresponding PCT/EP2015/072556 dated Jan. 28, 2016, two pages.

(Continued)

*Primary Examiner* — George Manuel
(74) *Attorney, Agent, or Firm* — Rankin, Hill & Clark LLP

(57) ABSTRACT

The invention relates to a method for supplying an electrical energy-converting implant with electrical energy, wherein an electrical voltage source is provided, wherein electrical voltage is generated by the linear movement of a piston of a free-piston generator.

20 Claims, 2 Drawing Sheets

(56) References Cited

U.S. PATENT DOCUMENTS

2013/0300345 A1* 11/2013 Trumbull .................. F03G 5/06
320/107
2014/0330069 A1* 11/2014 Hastings ............. A61M 1/1029
600/16

OTHER PUBLICATIONS

International Preliminary Report on Patentability for corresponding PCT/EP2015/072556 dated Apr. 13, 2017, nine pages.

* cited by examiner

PROCESS FOR SUPPLYING AN ELECTRICAL ENERGY CONVERTING IMPLANT WITH ELECTRICAL ENERGY

The present invention relates to a process for supplying an electrical energy converting implant with electrical energy by means of a free-piston generator.

Implants, which require energy to perform their intended function, are known. The most widespread example of such an implant is the heart pacemaker. In such a heart pacemaker, the pulse generator, which is responsible for the actual pacing, is connected to a one or two electrode system, which is inserted into the right atrium (in the case of sinus node impulse interference) or additionally into the right ventricle (in cases of disturbance of the atrioventricular conduction) is introduced and anchored via the vein. Implantation is usually performed in the upper right breast area (seen from the patient) below the collarbone. Recent developments also led to the miniaturisation of the known heart pacemakers, so that a direct implantation into the heart chamber is possible, whereby the electrodes are already part of the device.

However, all these devices have in common that they need electrical energy. By now lithium batteries, which can have a life span of several years, have been established for this. Afterwards an operation is required to replace the heart pacemaker, which encapsulates the battery. In the process the electrodes must be separated and a new electrode connection formed. Such an operation poses, in addition to the risk of infection associated with every operation, an additional burden on the patient. In particular, anesthesia as well as the psychological stress cannot be underestimated.

Therefore, there is a general need to provide a sustainable energy supply for such implants in order to minimize the above-mentioned risks.

In this context WO 2008/125866 A1, for example, energy generation within a living biological body is proposed. For this purpose, a pressure-sensitive device, which comprises a working fluid, is connected to an electrical generator and is adjusted in such a way that pressure changes within the working fluid are converted into electrical energy by a piston. The pressure changes are utilized by a device, which is arranged in the right ventricle of the heart or in a blood vessel. This device transfers the blood pressure fluctuations within the blood circulation in a mammal to the working fluid. The working fluid, in turn, drives the electrical generator by a linear movement, thereby generating electrical energy which can be supplied to an implant.

A disadvantage of this system is that the flow pulsation of the blood is only used pro rata. The additional insertion of the working fluid also reduces the efficiency. In addition, the presence of a working fluid always offers an additional risk of leaks and the like.

U.S. Pat. No. 3,563,245 describes a system in which a portion of the energy produced by the muscle contraction of the heart is supplied to a generator, which subsequently converts this energy into electrical energy. Again, a pressure-sensitive device is used which transmits movement energy to the generator through contractions via a working fluid (here a gas). The disclosed method is also disadvantageous for the reasons mentioned above.

Furthermore, there are currently theoretical considerations to generate electrical energy by using the heart pressure with a piezoelectric energy harvester. To date no practical implementations are known. However, also in these considerations only a small degree of efficiency can be achieved, which is a disadvantage.

The generation of electrical energy by means of a free-piston generator has already been known for many years. Its different configurations are therefore known to the person skilled in the art. They are characterized, in particular, by the compact design and the high power-to-weight ratio. A free-piston generator is a linear generator, which converts straight-lined motion energy into electrical energy.

The free-piston generator can also be used inversely as a free-piston engine. For example, U.S. Pat. No. 4,102,610 discloses the pumping of biological fluids by means of such an engine.

U.S. Pat. No. 3,788,772 proposes the use of a free-piston motor to power a heart machine during the operation of a patient's heart. Here, the free-piston engine takes over the heart's pumping function.

A similar Pumping function of the blood by a piston engine, although in miniaturized form, is also proposed in U.S. Pat. No. 5,879,375 and WO 03/034893 A2.

However, the problem of the sustainable energy supply of implants has not been satisfactorily solved to date.

Starting from this prior art, the task of the present invention is the elimination of at least one, preferably all, of the disadvantages of the prior art. In particular, the task of the present invention is to provide a process, in which an implant, which requires electrical energy, is supplied with electrical energy in a sustainable manner. The efficiency of the system should be at least as high, preferably higher than the systems described in the prior art.

These objects have been achieved by the process according to the invention, as described below.

According to the present invention, there is provided a process for supplying an electrical energy converting implant with electrical energy comprising the steps of:
(a) providing an electrical voltage source by generating electrical voltage by the linear movement of a piston 7 of a free-piston generator 2,
  wherein the free-piston generator 2 comprises a guide cylinder 6, in which a piston 7 with at least one permanent magnet is located, and at least one coil 8,
  the guide cylinder 6 is introduced into a blood vessel 1 and the at least one coil 8 is located outside the blood vessel 1,
  The piston 7 is being moved within the guide cylinder 6 of the free-piston engine 2 by the periodically pulsating blood in the blood vessel 1 linearly relative in the direction of the respective blood flow F, and
  as a function of this linear movement of the piston 7 an electrical voltage is induced in the at least one coil 8, and
(b) withdrawal of electrical energy from the electrical voltage source of step (a) by the current control unit of the electrical energy converting implant.

Process Step (a)

The free-piston generator 2 used according to the invention comprises a guide cylinder 6 and at least one coil 8. As already explained above, the general construction of a free-piston generator is known to a person skilled in the art.

According to the invention, the terms "comprise" and "contain" in one embodiment can also mean "consist of".

The guide cylinder 6 is a hollow cylinder which contains the piston 7. Preferably, the guide cylinder 6 comprises a polymer, which is selected from the group consisting of polymeric fluorinated hydrocarbons, polysiloxanes, polymeric organofunctionalized silanes and copolymers of the abovementioned polymers. Here, the guide cylinder 6 may preferably comprise a polymer as a coating selected from the group consisting of polymeric fluorinated hydrocarbons, polysiloxanes, polymeric organofunctionalized silanes and copolymers of the aforementioned polymers.

The polymeric fluorinated hydrocarbons are preferably fluorocarbons. Here, it is further preferred that the fluorocarbons are selected from the group consisting of polyvinyl tetrafluoride, polyvinylidene difluoride and polyvinylidene fluoride. Copolymers of fluorocarbons are preferably perfluoroalkoxy polymers (PFA) such as, for example, copolymers of tetrafluoroethylene and perfluoro-vinyl methyl ether.

The polysiloxanes are preferably polysiloxane resins, that is to say polysiloxanes having a respectively high degree of branching or linear polysiloxanes, for example hydrosilyl polydimethylsiloxane, which are subsequently crosslinked. Copolymers of polysiloxanes preferably comprise polyether polysiloxanes, polymethylsiloxane-polyalkylsiloxane, or polymethylsiloxane-polyalkylsiloxane-polyethers.

Among polymeric organofunctionalized silanes, the person skilled in the art will generally understand polymers comprising the following general structure (I):

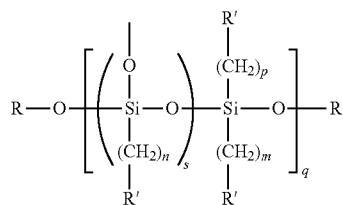

Thus, organofunctionalized silanes represent a subgroup of the copolymers of the polysiloxanes. The groups R' can be, in particular, functional groups selected from the group consisting of —$C_6H_5$, —SH, —$NH_2$, —$(CF_2)_5CF_3$, —$N^+Me_3Cl^-$, —O—$CH_2$—CH(O)$CH_2$, —CH=$CH_2$, —OC(O)CH=$CH_2$ and —OC(O)C($CH_3$)=$CH_2$. The numbers n, m and p can preferably be independently of one another 1 to 6 and s can preferably be 0 to 3. R is preferably H or —$CH_3$ and q is preferably 10000.

The polymer which the guide cylinder 6 can comprise can also contain further constituents, such as, for example, a low molecular weight crosslinker. The necessity or advantage of the incorporation of such further constituents is part of the knowledge of the person skilled in the art.

Likewise, the guide cylinder 6 can further exhibit a (additional) coating. This coating is preferably located on the outside of the guide cylinder 6, i.e., the side which comes into contact with blood. Coatings as well as surface treatments in order to adapt this outside of the guide cylinder to the application conditions, in particular the contact with blood, are known to the person skilled in the art.

Preferably, the guide cylinder has a wall thickness of 0.2 to 1.8 mm, particularly preferably of 0.5 to 1.5 mm and more preferably of 0.9 to 1.1 mm. Preferably, the guide cylinder 6 has an outer diameter of 2.5 to 7.5 mm, preferably 4 to 6 mm, particularly preferably substantially 5 mm. The guide cylinder preferably has a length (relative to the blood flow F) of 15 to 55 mm, particularly preferably 25 to 45 mm, more preferably 30 to 40 mm, especially preferably substantially 35 mm.

The guide cylinder 6 preferably has caps which can be attached, which are tapered towards the end, that is to say on the top surface and the base surface of the hollow cylinder (see FIG. 1). This simplifies the introduction of the guide cylinder into the blood vessel 1 by means of catheters. Likewise, the piston 7 is thereby held in the guide cylinder 6 and restricted in its movability. The attachable caps are preferably detachably mounted (e. g. by plug-, clip- or snap-fit-connections). Preferably, the inner ends of the guide cylinder 6 are positively adapted to the piston 7. For example, the inner ends, i.e., the inner top surface and base surface of the hollow cylinder, preferably have a concave shape.

The guide cylinder 7 is preferably arranged substantially axially symmetrically in the blood vessel (1). For the purpose of the present invention, the term "substantially" is used to permit slight deviations in principle. However, these deviations are preferably no more than 25%, more preferably no more than 10% and especially preferably not more than 5% of the actually stated value. On the whole, the guide cylinder 7 is thus preferably located in the center of the blood vessel 1 so that the blood in the blood vessel 1 can flow in a cylinder around the outer wall of the guide cylinder 7 up to the inner surface of the blood vessel 1 in the direction F (cf. FIG. 1).

It is furthermore preferred that the guide cylinder 7 is held by a tubular grid framework 4 which possesses at least one holder 5 for holding the guide cylinder. The tubular grid framework 4 is preferably a stent. This is known from the prior art. Such a tubular grid framework 4 is preferably used to introduce the guide cylinder into a blood vessel by means of catheter technology known to the person skilled in the art (eg catheter technique for balloon dilatation, as developed for percutaneous transluminal coronary angioplasty). Furthermore, this tubular grid framework 4 can additionally be expanded in a known manner with a balloon and thereby fix the guide cylinder 7 in the desired location in a blood vessel 1. This has in particular the advantage that the insertion of the free-piston generator 2 according to the invention can be carried out minimally invasive. As a result, the stress for the patient by the use of the free-piston generator 2 according to the invention is less than in the previously known techniques. The risk of infection is thereby reduced.

According to the invention, the guide cylinder (if applicable together with the tubular grid framework) is already introduced into a blood vessel. Thus, according to the invention, the step of introducing the guide cylinder into the blood vessel is excluded.

Preferably, the tubular grid framework 4 comprises a nickel-titanium alloy. Particularly preferably, the tubular grid framework 4 comprises nitinol. Especially preferably, the tubular grid framework 4 consists of nitinol.

Furthermore, the tubular grid framework 4 possesses at least one holder 5 for holding the guide cylinder 7. Such holders 5 are preferably formed in such a way that the blood flow F between the outer wall of the guide cylinder 7 and the inner wall of the blood vessel is restrained as little as possible. Thereby, the tubular grid framework 4 has as many holders as are required in order to hold the guide cylinder 7 firmly, i.e. to protect it against displacement with the blood flow F, and as little support as possible in order to reduce the influence on the blood flow F. Particularly preferably, this at least one holder 5 is a strut between the tubular grid framework 4 and the guide cylinder 7. More preferably the at least one strut 5 comprises or consists of the same material as the tubular grid framework 4.

The guide cylinder 6 comprises the piston 7. Thereby, it is preferred that the piston 7 is guided positively in the guide cylinder 6. The positive locking refers to the shape of the piston 7 longitudinal in relation to the blood flow F. Thus, the piston preferably has a cylindrical shape.

Preferably, the piston 7 essentially has a straight cylindrical shape with a circular base area, and a substantially hemispherical cap is positively placed on the base surface and, respectively, the top surface of the cylinder (see FIG. 1). Thereby it is particularly preferred that at least one of the substantially hemispherical caps has at least one opening. Preferably, both substantially hemispherical caps possess at least one opening.

Surprisingly, it turned out that these caps, which are placed on the piston 7, are suitable for controlled release of active substances. The at least one opening of the substantially hemispherical cap can thus be used for the controlled release of at least one active substance. This active substance is preferably selected from the group consisting of active substances which are usually administered intravenously. In particular, the active substance is selected from the group consisting of analgesics, antibiotics and anti-infectives. Preferably, at least one active substance is released, which minimizes thrombogenesis. More preferably, at least one active substance is released which is selected from the group consisting of heparin, acetylsalicylic acid, doxorubicin, TNT and any combinations thereof. In this case the use of TNT is advantageous as it has a blood pressure regulating effect. Likewise, the use of heparin and/or acetylsalicylic acid is advantageous because they have a blood thinning effect.

The kinetics of the release of the active substance can be controlled by a nanoperforation, preferably in the cylinder axis of the piston 7. The nanoperforation preferably has a defined circular cross-sectional area. The diameter of this surface is preferably 5 to 25 nm, particularly preferably 10 to 20 nm and especially preferably 14 to 16 nm. Preferably, this nanoperforation can be introduced into the caps by known lithographic methods. Thus, according to the invention, a nanocarrier, a nano-velo or a nano-container can also be provided.

Thereby, it is particularly preferred that at least one end of the guide cylinder 6 is removable (for example by a plug- or screw-connection). As a result, a replacement of the piston 7 after the complete release of the active substance with a new piston 7 in a minimally invasively manner is possible. In this way, a simple supply with the active substance is also possible.

Preferably, the piston 7 is sheathed with a polymer sheath. More preferably, the sheathing of the piston 7 comprises a polymer selected from the group consisting of polymeric fluorinated hydrocarbons, polysiloxanes, polymeric organofunctionalized silanes, and copolymers of the aforementioned polymers. These polymers have already been described above in more detail and, in particular, the abovementioned preferences also apply to the preferred materials of the polymer sheath of the piston 7.

The polymer, which may comprise the sheath of the piston 7, may further contain additional constituents, such as, for example, a low molecular weight crosslinker. The necessity respectively the advantage for the incorporation of such additional constituents is known by the person skilled in the art.

This sheathing preferably has a wall thickness of 0.01 to 0.2 mm, particularly preferably 0.05 to 0.15 mm, especially preferably 0.09 to 0.1 mm. This ensures that high biocompatibility, chemical stability and good sliding properties are achieved simultaneously.

The piston 7 possesses at least one permanent magnet. This means that it can comprise or consist of a permanent magnet. Particularly preferably, the piston 7 is a cylindrical permanent magnet with two attached caps, which are essentially hemispherical, as described above. Thereby, this overall system is preferably provided with the sheath described above.

More preferably, the permanent magnet is a rare earth super magnet. Particularly preferably, the permanent magnet is the ferromagnetic intermetallic compound $Nd_2Fe_{14}B$. It turned out that these have the requirements for high magnetic flux density $W_m=\frac{1}{2}B*H$ [$VAs/m^3=J/m^3$] by simultaneously high values of the remanence flux density $B_r$ of 1.4 T and the coercive field strength $H_c$ of 2000 kOe and is thus particularly suitable as a material for the piston 7 according to the invention.

The guide cylinder 6, which comprises the piston 7, if applicable with the tubular grid framework 4, is introduced into a blood vessel 1 as a complete system 3. The blood vessel 1 is preferably a vein.

It is particularly preferred that the complete system 3 and the at least one coil 8 are introduced into the "heart-close" right venous region. Here, "heart-close" is understood to mean, in particular, an area in which the diameter of the veins (internal diameter) is between 5 to 15 mm, preferably 8 to 12 mm, particularly preferably substantially 10 mm. The wall thickness of the vein in this area is in particular substantially 1.5 mm.

This position of the free-piston generator 2 is preferred, because a high flow velocity and a sufficient return flow velocity are present. A flow velocity of from 0.5 to 1.5 m/s, more preferably from 0.8 to 1.2 m/s, and especially preferably substantially 1 m/s, is preferably present at the transplant site. The period is preferably substantially 1 s. Furthermore, it is preferred that the pulsating return flow has a flow velocity of 0.1 to 0.5 m/s, particularly preferably 0.2 to 0.4 m/s, and especially preferably of substantially 0.3.

It is also possible to use the free-piston generator 2 according to the invention at a different location. As a support, a mechanical spring 9 can be introduced into the guide cylinder 6. This is particularly advantageous if this other implantation site has a very small or even too small pulsating return flow. This mechanical spring 9 thus provides support for the return movement of the piston 7 within the guide cylinder 6. This spring is preferably coated with polymer. This polymer is preferably selected from the group consisting of polymeric fluorinated hydrocarbons, polysiloxanes, polymeric organofunctionalized silanes and copolymers of the abovementioned polymers. These polymers have already been described in more detail above and in particular the above-mentioned preferences also apply to the materials preferred here.

The free-piston generator 2 further comprises at least one coil 8. This coil 8 is mounted outside the blood vessel 1, but essentially at the location at which the complete system 3 is located within the blood vessel 1. Thereby it is preferred that the complete system 3 within the blood vessel 1 and the at least one coil 8 extend in an axially symmetrical manner with respect to the blood vessel 1 (see FIG. 1).

The coil 8 is located outside the blood vessel 1. This means that it is not located in the blood flow F, but on the other side of the vessel wall where no blood flow takes place. Preferably, the coil is placed around the blood vessel 1.

The at least one coil 8 is preferably embedded in a sheathing or coil carrier. The jacket preferably consists of at least two (half) shells, which can be connected to one another in such a way that they close tightly and at the same time contact the coil windings with one another. Thus, it is possible to place the at least one coil 8 around a blood vessel 1 in a minimally invasive manner. The inner diameter of the at least one coil 8 is preferably 8 to 18 mm, particularly preferably 11 to 15 mm, especially preferably substantially 13 mm. This ensures that the blood vessel 1 is not damaged. The length of this sheath (in the direction relative to the blood flow F) is preferably 20 to 60 mm, particularly preferably 30 to 50 mm, more preferably 35 to 45 mm, especially preferably substantially 40 mm.

Preferably, the sheath comprises a polymer selected from the group consisting of polymeric fluorinated hydrocarbons, polysiloxanes, polymeric organofunctionalized silanes and copolymers of the aforementioned polymers. These polymers have already been described in more detail above and, in particular, the above-mentioned preferences also apply to the preferred materials of the sheath.

The polymer which the sheath may comprise may further contain additional constituents, such as, for example, a low molecular weight crosslinker. The necessity respectively the advantage for the incorporation of such additional constituents is known by the person skilled in the art.

An enclosure for magnetic shielding is preferably provided around the free-piston generator 2 according to the invention.

These spatially and physically described components above essentially form the free-piston generator 2 according to the invention. In the following, its mode of operation is described with reference to FIG. 1.

The temporal progressions of the flow velocity and pressure of the periodically pulsating (transient) blood flow have, in particular at the above-indicated preferred position, magnitudes which are sufficient for powering the free-piston generator 2 according to the invention.

If the blood flows firstly in one direction in the direction of the blood flow F, the piston 7 in the guide cylinder 6 is moved in the same direction as the blood flow. If the pulsation leads to a return flow in the opposite direction, the piston 7 in the guide cylinder 6 is likewise moved again in the opposite direction. This can be supported, as described above, by an additional mechanical coil (see FIG. 2). Overall, the pulsation of the blood is used to result in a linear reciprocation (relative to the blood flow F) of the piston 7 within the guide cylinder 6. The blood flow is thereby affected either by the heart itself and/or by an element supporting the blood flow, for example a heart pacemaker, wherein the blood flow-assisting element is first connected to a charged battery.

Therefore, the pulsation of the blood and not the pressure difference as described in the prior art are utilized for the described movement. As a result that the efficiency of the free-piston generator according to the invention is higher than the generators of the prior art. Thus, by direct transmission of the flow forces of the blood, an effective kinetic energy can be obtained. In addition, no additional working fluid is necessary, whereby further risks during an operation and especially risks of leakage are avoided.

The basic principle of the conversion of kinetic energy into electrical energy is known to the person skilled in the art. Depending on the linear movement of the magnetic piston 7, an electrical potential is induced in the at least one coil 8. Overall, an electrical potential is thus provided, which can be withdrawn from the free-piston generator 2 according to the invention.

In principle, the free-piston generator 2 according to the invention impedes the free blood flow F. Surprisingly, it could be shown that no adverse effects on the patient's health are to be expected by the process according to the invention.

Thereby, it is preferred that a proportionate residual diameter of the blood vessel 1 fulfills the following requirement:

$$1 > x_{rd} = d/D \geq \text{(greater than or equal to)}\ 0.5,$$

wherein
$x_{rd}$ represents the proportionate residual diameter of the blood vessel 1, which is available to the flow of the blood at the location of the blood vessel 1, on which the guide cylinder 6 of the free-piston generator 2 is fixed,
d represents the residual diameter of the blood vessel 1, which is available to the flow of the blood at the location of the blood vessel 1, on which the guide cylinder 6 of the free-piston generator 2 is fixed, and
D represents the total diameter of the blood vessel 1, whereby all diameters are inner diameters of the blood vessel 1.

This requirement was proved by calculations. In doing so, a venous blood flow was assumed. For simplicity, blood was regarded as a single-phase liquid having a density of 1060 kg/m$^3$ and considered as a Newtonian liquid bearing a constant viscosity. It was postulated that the numerous well-known and complex deviations from the reality will, to the greatest possible extent, average themselves out. The flow in a rigid tube was used as a basis.

The flow barrier was assumed to be an axially symmetrical object penetrating the wall with the shape of a half wave, whereby a length ratio and constriction ratio was being determined with respect to the free diameter D.

With a form factor of I/D=3.5 (where I represents the length of the obstacle), a reynolds number of approx. 530 and a frequency number of the non-stationary flow $S=(\rho*f*D^2)/\eta$ of approx. 10 were estimated.

The central diameter reduction by the guide cylinder 6 is, in comparison with the peripheral diameter reduction by the tubular grid framework 4, in the effect on the reduction of the cross-sectional area significantly lower.

The result of the mathematical modeling is based on the equations of motion and the continuity equation. As a whole, the flow velocity of the blood is increased by the generator, and the maximum flow velocity is increased by a factor of 1.5 in relation to the average flow velocity. This means that the differences in the flow velocities also increase.

Taking basic medical knowledge into account, it can be concluded that a health impairment is unlikely in a range of $1 > x_{rd} = d/D \geq 0.5$.

Process Step (b)

According to the invention in step (b) the withdrawal of electrical energy from the electrical voltage source of step (a) by the current control unit of the electrical energy converting implant takes place.

For this purpose, end contacts are attached to the coil 8. They serve as an interface to a wiring which leads to the electrical energy converting implant. In the implant itself, the electrical energy is preferably used, preferably after electronic stabilization, for charging or maintaining the rechargeable battery with which the implant is operated.

The withdrawal of energy and contacting of the electrical energy converting implant takes place according to the state of the art, for example via available line segments and connecting elements. There are current regulating elements or current control units which supply the implant with electrical energy in accordance with the demand.

Preferably, the electrical energy converting implant is a heart pacemaker.

Overall, the process according to the invention ensures a sustainable supply of an implant with electrical energy. In particular, operations for exchanging discharged batteries can be avoided. According to the invention, however, an exchange of the piston 7 for filling the active substance deposits can be provided. However, this intervention can be performed in a minimally invasive manner. Altogether, the risk of infection is significantly reduced. In addition, the psychological stress of a patient is significantly reduced with an electrical energy converting implant. Likewise, the need for anesthesia is thus reduced.

Preferably, the electrical energy converting implant is selected from the group consisting of a measuring chip, a control chip, a regulating chip, an implanted drug delivery unit, a micro-pump, and any combinations thereof. Thus, an online monitoring system or a diagnostic system can also be operated according to the invention. It is also possible to operate a pump for controlled drug release. Preferably, due to the high efficiency, several systems can be operated simultaneously.

In a further aspect of the present invention, there is provided a device for carrying out the method described above. With regard to the physical characteristics of the device, reference is made to the statements above regarding the process according to the invention. In particular, it is a device comprising (a) An electrical voltage source which generates electrical voltage by the linear movement of a piston (7) of a free-piston generator (2), wherein the free-piston generator (2) comprises a guide cylinder (6), in which there is a piston (7) with at least one permanent magnet, and at least one coil (8), The guide cylinder (6) is inserted into a blood vessel (1), and the at least one coil (8) is located outside of the blood vessel (1)

The piston (7) is designed such that it can be moved linearly relative to the respective blood flow (F) within the guide cylinder (6) of the free piston motor (2) by the periodically pulsating blood in the blood vessel (1), and an electric voltage is induced in the at least one coil (8) as a function of this linear movement of the piston (7), and (b) an electrical energy converting implant comprising a current control unit, which is adapted to withdraw the electrical energy from the electrical voltage source.

In the device according to the invention, the piston (7) is preferably guided positively in the guide cylinder (6).

In a further aspect of the current invention

Furthermore, it is preferred if the guide cylinder (7) is arranged essentially axially symmetrically in the blood vessel (1) and is thereby held by a tubular grid framework (4) which possesses at least one holder (5) for holding the guide cylinder.

The bloods vessel is generally a vein.

The proportionate residual diameter of the blood vessel (1) preferably fulfills the following requirement:

$$1 > x_{rd} = d/D \geq 0.5,$$

wherein $x_{rd}$ represents the proportionate residual diameter of the blood vessel (1), which is available to the flow of the blood at the location of the blood vessel (1), on which the guide cylinder (6) of the free-piston generator (2) is fixed, d represents the residual diameter of the blood vessel (1), which is available to the flow of the blood at the location of the blood vessel (1), on which the guide cylinder (6) of the free-piston generator (2) is fixed, and D represents the total diameter of the blood vessel (1), whereby all diameters are inner diameters of the blood vessel (1).

Preferably, the piston (7) essentially has a straight cylindrical shape with a circular base area, and a substantially hemispherical cap is positively placed on the base surface and, respectively, the top surface of the cylinder.

REFERENCE LIST

1 Blood vessel
2 Free-piston generator
3 complete system, which is introduced into the interior of the blood vessel 1
4 tubular grid framework
5 holder
6 guide cylinder
7 piston
8 coil
9 spring
F direction of the blood flow

Figure 1:
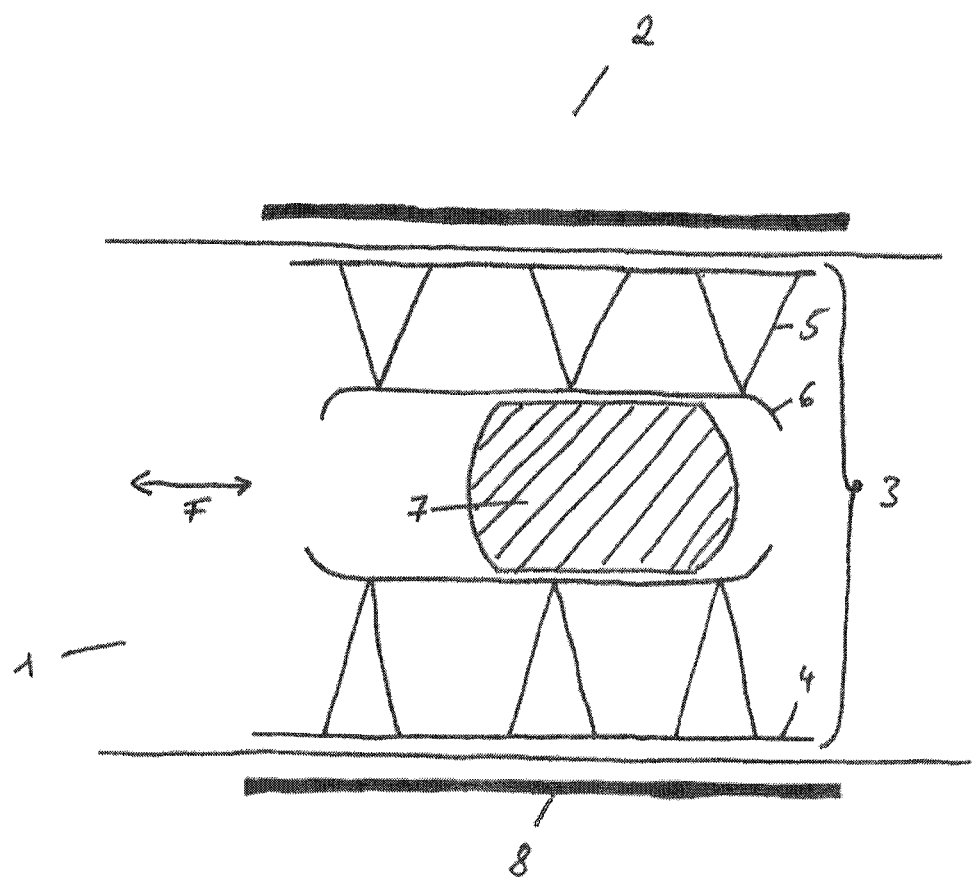
FIG. 1: Shows a longitudinal section through a blood vessel 1 into which a free-piston generator is integrated. The holders 5 are struts between the outer side of the guide cylinder 6 and the tubular grid framework 4. The guide cylinder 6 is introduced essentially axially symmetrically into the blood vessel 1. The piston 7 possesses two hemispherical caps.
Figure 2:
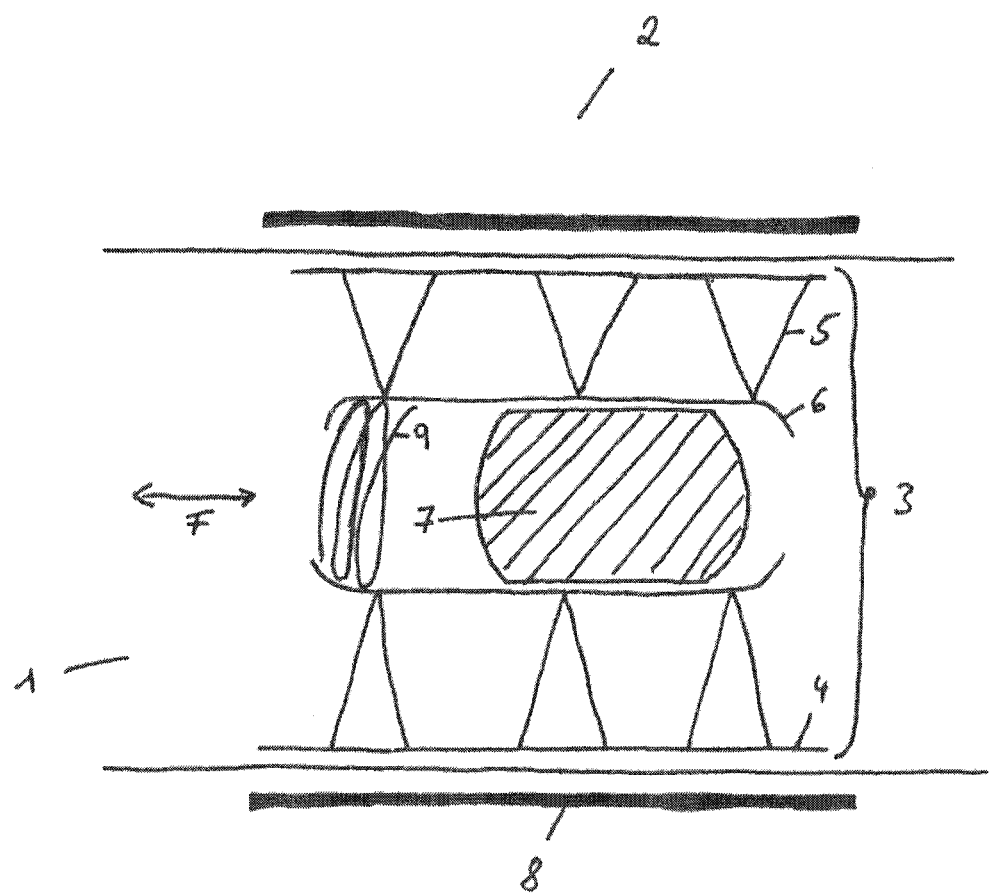
FIG. 2: Basically corresponds to FIG. 1, whereby additionally a spring 9 is integrated into the guide cylinder 6.

The invention claimed is:

1. A process for supplying an electrical energy converting implant with electrical energy comprising the steps of:

(a) providing an electrical voltage source by generating electrical voltage by the linear movement of a piston 7 of a free-piston generator 2, wherein the free-piston generator 2 comprises a guide cylinder 6, in which a piston 7 with at least one permanent magnet is located, and at least one coil 8, the guide cylinder 6 is introduced into a blood vessel 1 and the at least one coil 8 is located outside the blood vessel 1, the piston 7 is being moved within the guide cylinder 6 of the free-piston engine 2 by the periodically pulsating blood in the blood vessel 1 linearly relative in the direction of the respective blood flow F, and as a function of this linear movement of the piston 7 an electrical voltage is induced in the at least one coil 8, and (b) withdrawal of electrical energy from the electrical voltage source of step (a) by the current control unit of the electrical energy converting implant.

2. The process according to claim 1, whereby the piston 7 is guided positively in the guide cylinder 6.

3. The process according to claim 1, wherein the guide cylinder 6 is arranged essentially axially symmetrically in the blood vessel 1 and is thereby held by a tubular grid framework 4 which possesses at least one holder 5 for holding the guide cylinder.

4. The process according to claim 1, wherein the blood vessel 1 is a vein.

5. The process according to claim 1, wherein a proportionate residual diameter of the blood vessel 1 fulfills the following requirement:

$$1 > x_{rd} = d/D \geq 0.5,$$

wherein $x_{rd}$ represents the proportionate residual diameter of the blood vessel 1, which is available to the flow of the blood at the location of the blood vessel 1, on which the guide cylinder 6 of the free-piston generator 2 is fixed, d represents the residual diameter of the blood vessel 1, which is available to the flow of the blood at the location of the blood vessel 1, on which the guide cylinder 6 of the free-piston generator 2 is fixed, and D represents the total diameter of the blood vessel 1, whereby all diameters are inner diameters of the blood vessel 1.

6. The process according to claim 1, wherein the piston 7 of the free-piston generator 2 essentially has a straight cylindrical shape with a circular base area, and a substantially hemispherical cap is positively placed on the base surface and, respectively, the top surface of the cylinder.

7. The process according to claim 6, wherein at least one of the substantially hemispherical caps possesses at least one opening.

8. The process according to claim 7, wherein the at least one opening can be used for the controlled release of at least one active substance.

9. The process according to claim 1, wherein the electrical energy converting implant is a heart pacemaker.

10. The process according to claim 1, wherein the electrical energy converting implant is selected from the group consisting of a measuring chip, a control chip, a regulating chip, an implanted drug delivery unit, a micro-pump, and any combinations thereof.

11. A device comprising
(a) an electrical voltage source which generates electrical voltage by the linear movement of a piston 7 of a free-piston generator 2,
  wherein the free-piston generator 2 comprises a guide cylinder 6, in which there is a piston 7 with at least one permanent magnet, and at least one coil 8,
  wherein the guide cylinder 6 is adapted to be inserted into a blood vessel 1, and the at least one coil 8 is located outside of the blood vessel 1,
  wherein the piston 7 is designed such that it can be moved linearly relative to the respective blood flow F within the guide cylinder 6 of the free piston motor 2 by a periodically pulsating blood in the blood vessel 1, and
  an electric voltage is induced in the at least one coil (8) as a function of this linear movement of the piston (7), and
(b) an electrical energy converting implant comprising a current control unit, which is adapted to withdraw the electrical energy from the electrical voltage source.

12. The device according to claim 11, wherein the piston 7 is guided positively in the guide cylinder 6.

13. The device according to claim 11, wherein the guide cylinder 6 is adapted to be arranged essentially axially symmetrically in the blood vessel 1 and is thereby held by a tubular grid framework 4 which possesses at least one holder 5 for holding the guide cylinder.

14. The device according to claim 11, wherein the blood vessel 1 is a vein.

15. The device according to according to claim 11, wherein a proportionate residual diameter of the blood vessel 1 fulfills the following requirement:

$$1 > x_{rd} = d/D \geq 0.5,$$

wherein $x_{rd}$ represents the proportionate residual diameter of the blood vessel 1, which is available to the flow of the blood at the location of the blood vessel 1, on which the guide cylinder 6 of the free-piston generator 2 is fixed, d represents the residual diameter of the blood vessel 1, which is available to the flow of the blood at the location of the blood vessel 1, on which the guide cylinder 6 of the free-piston generator 2 is fixed, and D represents the total diameter of the blood vessel 1, whereby all diameters are inner diameters of the blood vessel 1.

16. The device according to claim 11, wherein the piston 7 of the free-piston generator 2 essentially has a straight cylindrical shape with a circular base area, and a substantially hemispherical cap is positively placed on the base surface and the top surface of the cylinder.

17. The device according to claim 16, wherein at least one of the substantially hemispherical caps possesses at least one opening.

18. The device according to claim 17, wherein the at least one opening can be used for the controlled release of at least one active substance.

19. The device according to claim 11, wherein the electrical energy converting implant is a heart pacemaker.

20. The device according to claim 11, wherein the electrical energy converting implant is selected from the group consisting of a measuring chip, a control chip, a regulating chip, an implanted drug delivery unit, a micro-pump, and combinations thereof.

* * * * *